United States Patent [19]

Eilingsfeld et al.

[11] Patent Number: 4,785,116
[45] Date of Patent: Nov. 15, 1988

[54] AMINOISOTHIAZOLE COMPOUNDS

[75] Inventors: Heinz Eilingsfeld; Karl-Heinz Etzbach, both of Frankenthal, Fed. Rep. of Germany

[73] Assignee: BASF Aktiengesellschaft, Rheinland-Pfalz, Fed. Rep. of Germany

[21] Appl. No.: 692,524

[22] Filed: Jan. 18, 1985

[30] Foreign Application Priority Data

Jan. 21, 1984 [DE] Fed. Rep. of Germany ....... 3402024

[51] Int. Cl.$^4$ ................. C07D 275/02; C07D 275/06; C07D 513/04
[52] U.S. Cl. .................................... 548/212; 544/235; 548/214
[58] Field of Search ............... 548/207, 209, 212, 214; 544/235

[56] References Cited

U.S. PATENT DOCUMENTS

| | | | |
|---|---|---|---|
| 3,155,678 | 11/1964 | Hatchard | 71/90 |
| 3,551,442 | 12/1970 | Guillot et al. | 71/90 |
| 3,562,285 | 2/1971 | Gadekar et al. | 548/212 |
| 3,622,593 | 11/1971 | Volpp et al. | 71/90 |
| 3,699,115 | 10/1972 | Franz | 548/214 |
| 4,079,050 | 3/1978 | Baird et al. | 534/783 |
| 4,092,329 | 5/1978 | Jotterand | 549/61 |
| 4,108,867 | 8/1978 | Baird et al. | 549/68 |
| 4,211,696 | 7/1980 | Baird et al. | 549/68 X |
| 4,490,541 | 12/1984 | Eilingsteld et al. | 548/370 |
| 4,593,087 | 6/1986 | Gourley | 543/784 |

FOREIGN PATENT DOCUMENTS 3402024 7/1985 Fed. Rep. of Germany ...... 548/212
1516777 3/1968 France .

OTHER PUBLICATIONS

Holland et al., J. Chem. Soc. [1965], pp. 7277-7282.
Goerdeler et al., Chem. Ber., vol. 102, 2273-2284 (1969).
Imahori et al., Chemical Abstracts, vol. 88, 75295a (1978).
Gewald et al., Chemical Abstracts, vol. 92, 76382w (1980).
Adams et al., "Isothiazole: A New Mononuclear Heterocyclio System," *Chem. Abst.* 54: 12113-12115 (1959).
Gardner et al., "The Synthesis in Hydrazine Derivatives," *Chem. Abst.* 51:3610-3611 (1957).
Journal of the American Chemical Society, Band 80, Nr. 6, 20. Mar. 1958, Easton, Penn., U.S.A.; R. H. Wiley et al., "Carbamylmaleimides from the Malonamide-Diethyl Oxalate Reaction" pp. 1385-1388.
Robba et al., *Bulletin de la Société Chimique de France*, No. 5 (1969), pp. 1762-1768.

*Primary Examiner*—Donald G. Daus
*Assistant Examiner*—Diana G. Rivers
*Attorney, Agent, or Firm*—Oblon, Fisher, Spivak, McClelland & Maier

[57] ABSTRACT

Novel compounds of the general formula I

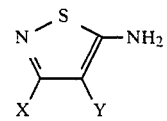

where X and Y independently of one another are each carboxyl, a carboxylic ester group, cyano or an unsubstituted or substituted carbamyl or carboxylic hydrazide group and X and Y together form a radical of the formula

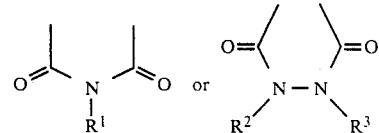

where $R^1$ is hydrogen or a radical of a primary amine and $R^2$ and $R^3$ are each hydrogen or unsubstituted or substituted alkyl, cycloalkyl or aryl, are very useful as diazo components.

7 Claims, No Drawings

AMINOISOTHIAZOLE COMPOUNDS

The present invention relates to compounds of the general formula I

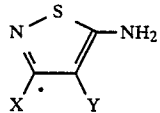

where X and Y independently of one another are each carboxyl, a carboxylic ester group, cyano or an unsubstituted or substituted carbamyl or carboxylic hydrazide group and X and Y together form a radical of the formula

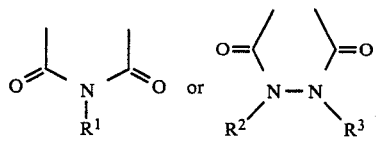

where $R^1$ is hydrogen or a radical of a primary amine, and $R^2$ and $R^3$ are each hydrogen or unsubstituted or substituted alkyl, cycloalkyl or aryl.

Examples of carboxylic ester groups X and Y are $C_1$–$C_{12}$-alkoxycarbonyl, cyclohexyloxycarbonyl, allyloxycarbonyl, 2-($C_1$–$C_4$-alkoxy)-ethoxycarbonyl, 3-($C_1$–$C_4$-alkoxy)-propoxycarbonyl, 2-phenoxyethoxycarbonyl, 3-phenoxypropoxycarbonyl, phenylmethoxycarbonyl, 2-phenylethoxycarbonyl, phenoxycarbonyl which is unsubstituted or substituted by chlorine, bromine, nitro or cyano, $C_1$–$C_4$-alkylphenoxycarbonyl, dimethylphenoxycarbonyl or trimethylphenoxycarbonyl.

Examples of carbamyl radicals X and Y are $C_1$–$C_{12}$-alkylcarbamyl, cyclohexylcarbamyl, allylcarbamyl, 2-($C_1$–$C_4$-alkoxy)-ethylcarbamyl, 3-($C_1$–$C_4$-alkoxy)-propylcarbamyl, 2-phenoxyethylcarbamyl, 3-phenoxypropylcarbamyl, phenylmethylcarbamyl, 2-phenylethylcarbamyl, phenylcarbamyl which is unsubstituted or substituted by chlorine, bromine, nitro or cyano, $C_1$–$C_4$-alkylphenylcarbamyl, dimethylphenylcarbamyl, trimethylphenylcarbamyl, $C_1$–$C_4$-dialkylcarbamyl, methylcyclohexylcarbamyl, dicyclohexylcarbamyl or a radical of the formula

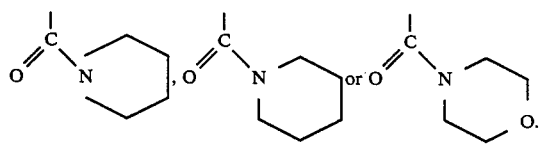

Examples of carboxylic hydrazide radicals are

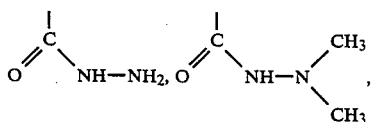

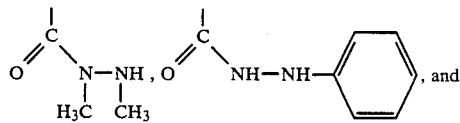

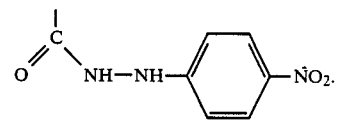

When the carbamyl compounds are prepared by opening the ring

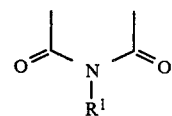

the group of the formula —$CONHR^1$ is retained while the second carbamyl group, which corresponds to either X or Y, is formed with the amine used for the ring cleavage.

Corresponding statements apply to the esters, acids and hydrazides.

$R^1$ is, for example, hydrogen, $C_1$–$C_{12}$-alkyl, cyclohexyl, allyl, 2-($C_1$–$C_4$-alkoxy)-ethyl, 3-($C_1$–$C_4$-alkoxy)-propyl, 2-phenoxyethyl, 3-phenoxypropyl, phenylmethyl, phenylethyl, phenyl which is unsubstituted or substituted by chlorine, bromine, cyano or nitro, $C_1$–$C_4$-alkylphenyl, dimethylphenyl or trimethylphenyl.

$R^2$ and $R^3$ are each, for example, hydrogen or $C_1$–$C_{12}$-alkyl, and one of the radicals may furthermore be phenyl which is unsubstituted or substituted by chlorine, bromine, cyano or nitro.

The compounds of the formula I can be prepared if a compound of the formula

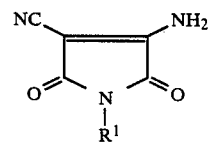

which is obtainable by reacting a compound of the formula

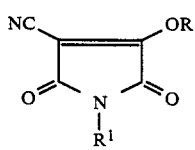

with ammonia, is reacted with a dithiophosphate; this initially gives a compound of the formula

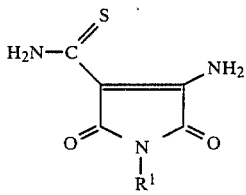

which can be converted to the isothiazole compound by a conventional method, for example by reaction with $H_2O_2$ in glacial acetic acid.

Compounds of the formula III can be obtained by methods similar to those stated in J. Am. Chem. Soc. 80 (1958), 1385 for the compound of the formula

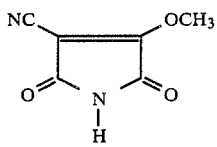  V and in German Laid-Open Application DOS No. 3,204,713 for the compound of the formula

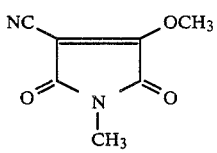  VI

The Examples which follow illustrate typical preparations. Parts and percentages are by weight, unless stated otherwise.

The compounds of the formula I can be diazotized and are therefore useful as, for example, diazo components.

Of particular importance are compounds of the formula I in which X and Y are each CN or $CONHB^1$, where the radicals $B^1$ are identical or different and are each hydrogen, $C_1$–$C_{12}$-alkyl or phenyl. Furthermore, X and Y together preferably form the radical of the formula

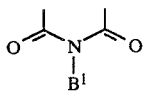

where $B^1$ has the stated meanings.

Other useful compounds are those of the formula

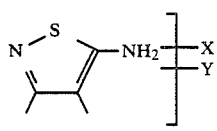

where X is $CONHB^1$ and Y is di-($C_1$–$C_{12}$-alkyl)-carbamyl, carboxyl, $C_1$–$C_{12}$-alkoxycarbonyl, phenoxycarbonyl or a radical of the formula

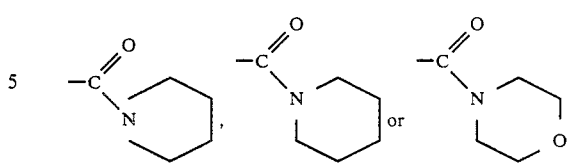

and $B^1$ has the stated meanings.

EXAMPLE 1

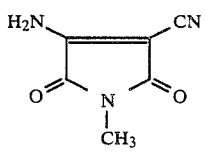

120 parts of 2-cyano-3-methoxy-N-methylmaleimide are dissolved in 600 parts of methylglycol and 13.5 parts of ammonia are then passed into the ice-cooled solution. Stirring is then continued for 3 hours at room temperature, and the resulting precipitate is filtered off under suction, washed with methanol and then with water, and dried to give 90 parts (83% of theory) of 3-amino-2-cyano-N-methylmaleimide.

mp.: 284° C. (methylglycol), IR (KBr): 3285, 3122 ($NH_2$), 2220 (C≡N), 1780, 1725, 1605 cm$^{-1}$ (C=O), $C_6H_5N_3O_2$ (151.13).

Calculated: C 47.69, H 3.33, N 27.80, O 21.17; Found: C 47.6, H 3.5, N 27.5, O 21.7.

EXAMPLE 2

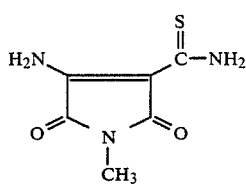

A mixture of 100 parts of phosphorus pentasulfide and 450 parts of methylglycol is heated at the boil for 0.5 hour, after which 90 parts of 3-amino-2-cyano-N-methylmaleimide are introduced into this solution at 100° C. The mixture is stirred for 3 hours at 100° C. and then overnight at room temperature. The resulting precipitate is filtered off under suction, washed with methanol and then with water, and dried to give 65.1 parts (59% of theory) of 3-amino-2-thiocarbamyl-N-methylmaleimide.

mp.: 282° C. (methylglycol), IR (KBr): 3390, 3280 ($NH_2$), 1760, 1700, 1625 cm$^{-1}$ (C=O), $C_6H_7N_3O_2S$ (185.21).

Calculated: C 38.91, H 3.81, N 22.69, O 17.28, S 17.31; Found: C 38.9, H 3.6, N 22.8, O 17.3, S 17.4.

EXAMPLE 3

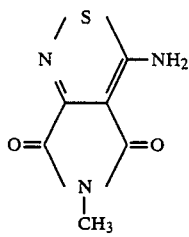

38.3 parts of a 30% strength aqueous hydrogen peroxide solution are added dropwise to a mixture of 62.5 parts of 3-amino-2-thiocarbamyl-N-methylmaleimide and 300 parts of glacial acetic acid, the temperature being kept at 30°–40° C. during this procedure by cooling. The mixture is then stirred for a further 2 hours at room temperature, and the resulting precipitate is filtered off under suction, washed with glacial acetic acid and then with water, and dried to give 54.5 parts (88% of theory) of 5-aminoisothiazole-3,4-N-methyldicarboximide.

mp.: 242° C. (glacial acetic acid), IR (KBr): 3420, 3313 (NH$_2$), 1763, 1705, 1611 cm$^{-1}$ (C=O), C$_6$H$_5$N$_3$O$_2$S (183.19).

Calculated: C 39.34, H 2.75, N 22.94, O. 17.47, S 17.50; Found: C 39.5, H 2.9, N 23.2, O 17.5, S 17.4.

EXAMPLE 4

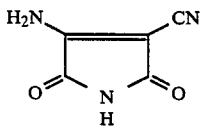

The compound is prepared as described in Example 1, from 217 parts of 2-cyano-3-methoxymaleimide, 1,000 parts of isopropanol and 26.7 parts of ammonia. Yield: 192 parts (89% of theory) of 3-amino-2-cyanomaleimide.

Decomposition temperature: 260° C. (H$_2$O), IR (KBr): 3275, 3120 (NH$_2$), 2220 (C≡N), 1782, 1725, 1650 cm$^{-1}$ (C=O), C$_5$H$_3$N$_3$O$_2$ (137.10).

Calculated: C 43.80, H 2.21, N 30.65, O 23.34; Found: C 43.9, H 2.3, N 30.5, O 23.4.

EXAMPLE 5

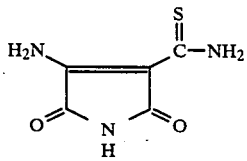

The compound is prepared as described in Example 2, from 125 parts of phosphorus pentasulfide, 600 parts of n-butanol and 102.8 parts of 3-amino-2-cyanomaleimide. Yield: 61 parts (48% of theory) of 3-amino-2-thiocarbamylmaleimide.

Decomposition temperature: 262° C. (n-butanol), IR (KBr): 3366, 3320, 3191 (NH$_2$), 1762, 1719, 1644, 1610 cm$^{-1}$ (C=O), C$_5$H$_5$N$_3$O$_2$S (171.18).

Calculated: C 35.08, H 2.94, N 24.55, O 18.69, S 18.73; Found: C 35.4, H 3.1, N 24.2, O 18.9, S 18.7.

EXAMPLE 6

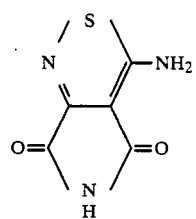

The compound is obtained as described in Example 3, from 75.2 parts of 3-amino-2-thiocarbamylmaleimide, 400 parts of acetic acid and 50 parts of a 30% strength aqueous hydrogen peroxide solution. Yield: 68 parts (91% of theory) of 5-aminoisothiazole-3,4-dicarboximide.

Decomposition temperature: 268° C. (methylglycol), IR (KBr): 3419, 3220, 3142 (NH, NH$_2$), 1764, 1714, 1691 cm$^{-1}$ (C=O), C$_5$H$_3$N$_3$O$_2$S (169.16).

Calculated: C 35.50, H 1.79, N 24.84, O 18.92, S 18.95; Found: C 35.4, H 2.0, N 24.8, O 18.5, S 18.7.

EXAMPLE 7

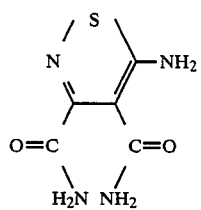

A mixture of 10.1 parts of 5-aminoisothiazole-3,4-dicarboximide and 70 parts of concentrated aqueous ammonia solution is stirred for 2 hours at room temperature, and the colorless precipitate is then filtered off under suction, washed with water and dried to give 9.3 parts (83% of theory) of 5-aminoisothiazole-3,4-dicarboxamide.

mp.: 205° C. (water), IR (KBr): 3400, 3330, 3275, 3140 (NH$_2$), 1680, 1668, 1655 cm$^{-1}$ (C=O), C$_5$H$_6$N$_4$O$_2$S (186.19).

Calculated: C 32.25, H 3.25, N 30.09, O 17.19, S 17.22; Found: C 32.3, H 3.1, N 30.4, O 17.2, S 17.4.

EXAMPLE 8

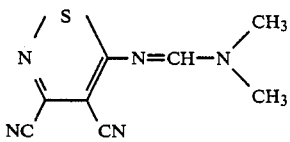

10.1 parts of phosphorus oxytrichloride are added dropwise to 30 parts of dimethylformamide at 0° C., and the mixture is then stirred for a further 0.5 hour at this temperature. 3.7 parts of 5-aminoisothiazole-3,4-dicarboxamide are then introduced, a little at a time, into this solution while cooling with ice. The mixture is stirred for a further 2 hours at room temperature, after which it is poured into 100 parts of ice water. The precipitate is filtered off under suction, washed with water and dried to give 3.8 parts (93% of theory) of N,N-dimethyl-N'-(3,4-dicyanoisothiazol-5-yl)-formamidine.

mp.: 173° C. (n-butanol), IR (KBr): 2210 (C≡N), 1625 cm⁻¹ (C=N), C₈H₇N₅S (205.24).

Calculated: C 46.82, H 3.44, N 34.12, S 15.62; Found: C 46.5, H 3.1, N 34.1, S 15.7.

EXAMPLE 9

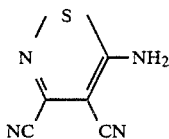

A mixture of 45.3 parts of N,N-dimethyl-N'-(3,4-dicyanoisothiazol-5-yl)-formamidine, 400 parts of ethanol and 60 parts of concentrated hydrochloric acid is heated at the boil for 2.5 hours, after which it is introduced into 400 parts of water. The colorless precipitate is filtered off under suction, washed with water and dried to give 28.6 parts (87% of theory) of 5-aminoisothiazole-3,4-dicarbonitrile.

Decomposition temperature: 240° C. (glacial acetic acid).

IR (KBr): 3380, 3290, 3190 (NH₂), 2210 (C≡N), C₅H₂N₄S (150.16).

Calculated: C 39.99, H 1.34, N 37.31, S 21.35; Found: C 40.1, H 1.6, N 37.3, S 21.1.

EXAMPLE 10

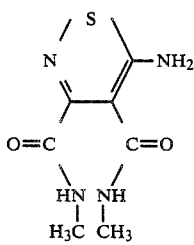

Methylamine is passed into 50 parts of methanol at room temperature until the solution is saturated, 4.6 parts of 5-aminoisothiazole-3,4-N-methyldicarboximide are introduced and the mixture is then stirred for 3 hours at room temperature. The clear solution is then poured into 100 parts of water, and the precipitate is filtered off under suction, washed with water and dried to give 4.3 parts (80% of theory) of 5-aminoisothiazole-3,4-di-N-methylcarboxamide.

mp.: 222° C. (n-butanol), IR (KBr): 3400, 3350, 3220 (NH₂, NH), 1645, 1590 cm⁻¹ (C=O), C₇H₁₀N₄O₂S (214.25).

Calculated: C 39.24, H 4.70, N 26.15, O 14.94, S 14.97; Found: C 39.5, H 4.6, N 26.1, O 15.2, S 15.0.

EXAMPE 11

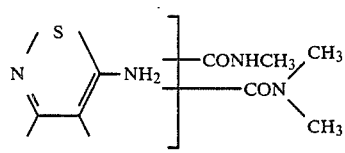

Dimethylamine is passed into 50 parts of methanol at room temperature until the solution is saturated, 10.1 parts of 5-aminoisothiazole-3,4-N-methyldicarboximide are then introduced and the mixture is stirred for 1.5 hours at room temperature. 1 part of animal charcoal is then added, and the mixture is filtered. The filtrate is evaporated to dryness under reduced pressure, and the oil which remains is freed from residual solvent under reduced pressure. 12.1 parts (97% of theory) of a red oil which gradually crystallizes are obtained.

mp.: 116° C. (toluene), IR (KBr): 3401, 3255 (NH, NH₂), 1636, 1622, 1608, 1595 cm⁻¹ (C=O), C₈H₁₂N₄O₂S (228.27).

Calculated: C 42.09, H 5.30, N 24.54, O 14.02, S 14.05; Found: C 42.3, H 5.4, N 24.2, O 14.3, S 13.7.

EXAMPLE 12

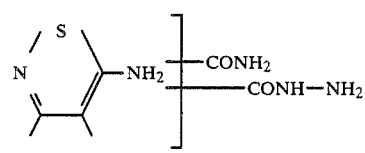

A mixture of 10.1 parts of 5-aminoisothiazole-3,4-dicarboximide, 3.3 parts of hydrazine hydrate and 50 parts of water is heated at the boil for 0.5 hour. When the mixture has cooled to room temperature, the resulting precipitate is filtered off under suction, washed with water and dried to give 10.5 parts (87% of theory) of a compound of the above formula.

Decomposition temperature: 206° C. (water), IR (KBr): 3359, 3301, 3248 (NH, NH₂), 1637, 1614 cm⁻¹ (C=O), C₅H₇N₅O₂S (201.21).

Calculated: C 29.85, H 3.51, N 34.81, O 15.90, S 15.94; Found: C 29.6, H 3.3, N 34.5, O 16.0, S 16.1.

EXAMPLE 13

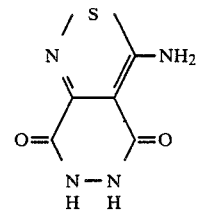

11.5 parts of the compound of Example 14 in 200 parts of glacial acetic acid are heated at the boil for 10 hours. When the mixture has cooled, the precipitate is filtered off under suction, washed with glacial acetic acid and dried to give 7 parts (67% of theory) of 7-amino-3,4,5,6-tetrahydro-3,6-dioxopyridazino[4,5-c]isothiazole.

mp.: >300° C., IR (KBr): 3417, 3220 (NH, NH₂), 2800 very broad (NH/OH), 1641 cm⁻¹ (C=O), C₅H₄N₄O₂S (184.18).

Calculated: C 32.61, H 2.19, N 30.42, O 17.37, S 17.41; Found: C 32.8, H 2.2, N 30.0, O 17.8, S 17.1.

We claim:
1. A compound of the formula:

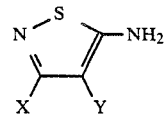

wherein X and Y independently are each a carboxyl group, a cyano group, a carboxylic ester group selected from the group consisting of $C_1$-$C_{12}$-alkoxycarbonyl, cyclohexyloxycarbonyl, allyloxycarbonyl, 2-($C_1$-$C_4$-alkoxy)-ethoxycarbonyl, 3-($C_1$-$C_4$-alkoxy)propoxycarbonyl, 2-phenoxyethoxycarbonyl, 3-phenoxypropoxycarbonyl, phenylmethoxycarbonyl, 2-phenylethoxycarbonyl, phenoxycarbonyl which is unsubstituted or substituted by chlorine, bromine, nitro or cyano; $C_1$-$C_4$-alkylphenoxycarbonyl, dimethylphenoxycarbonyl or a trimethylphenoxycarbonyl group; a carbamyl group which is unsubstituted or substituted and which is selected from the group consisting of $C_1$-$C_{12}$-alkylcarbamyl, cyclohexylcarbamyl, allylcarbamyl, 2-($C_1$-$C_4$-alkoxy)-ethylcarbamyl, 3-($C_1$-$C_4$-alkoxy)-propylcarbamyl, 2-phenoxyethylcarbamyl, 3-phenoxypropylcarbamyl, phenylmethylcarbamyl, 2-phenylethylcarbamyl, phenylcarbamyl which is unsubstituted or substituted by chlorine, bromine, nitro or cyano; $C_1$-$C_4$-alkyphenylcarbamyl, dimethylphenylcarbamyl, trimethylphenylcarbamyl, $C_1$-$C_4$-dialkylcarbamyl, methycyclohexylcarbamyl, and dicyclohexylcarbamyl; or a carboxylic hydrazide group selected from the group consisting of:

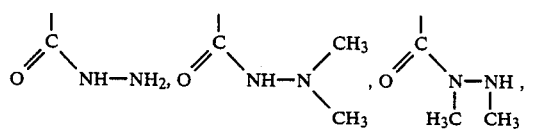

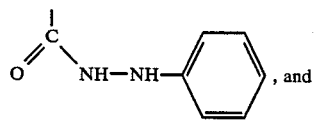

or X and Y together form a radical of the formula:

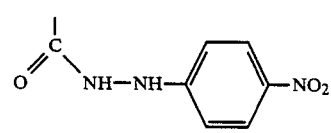

wherein $R^1$ is a group selected from the group consisting of hydrogen, $C_1$-$C_{12}$-alkyl, cyclohexyl, allyl, 2-($C_1$-$C_4$-alkoxy)ethyl, 3-($C_1$-$C_4$-alkoxy)-propyl, 2-phenoxyethyl, 3-phenoxypropyl, phenylmethyl, phenylethyl, phenyl which is unsubstituted or substituted by chlorine, bromine, cyano or nitro, $C_1$-$C_4$-alkylphenyl, dimethylphenyl or trimethylphenyl and $R^2$ and $R^3$ are independently hydrogen or $C_1$-$C_{12}$-alkyl, or one of $R^2$ and $R^3$ is phenyl which is unsubstituted or substituted by chlorine, bromine, cyano or nitro.

2. The compound as claimed in claim 1, wherein X and Y are each a carboxylic ester group selected from the group consisting of $C_1$-$C_{12}$-alkoxycarbonyl, cyclohexyloxycarbonyl, allyloxycarbonyl, 2-($C_1$-$C_4$-alkoxy)-ethoxycarbonyl, 3-($C_1$-$C_4$-alkoxy)propoxycarbonyl, 2-phenoxyethoxycarbonyl, 3-phenoxypropoxycarbonyl, phenoxymethoxycarbonyl, and phenoxycarbonyl which is unsubstituted or substituted by chlorine, bromine, nitro or cyano; $C_1$-$C_4$-alkoxyphenoxycarbonyl, dimethylphenoxycarbonyl or trimethylphenoxycarbonyl.

3. The compound as claimed in claim 1, wherein X and Y each are cyano or —$CONHB^1$, wherein $B^1$ is hydrogen, phenyl or a $C_1$-$C_{12}$-alkyl group.

4. The compound as claimed in claim 1, wherein X and Y together form a radical of the formula;

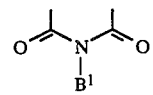

wherein $B^1$ is hydrogen, phenyl or a $C_1$-$C_{12}$-alkyl group.

5. A compound of the formula:

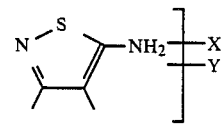

wherein X is —$CONHB^1$ and Y is di-($C_1$-$C_{12}$-alkyl)-carbamyl, carboxyl, $C_1$-$C_{12}$-alkoxycarbonyl, phenoxycarbonyl or a radical of the formula:

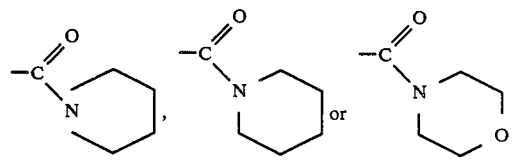

wherein $B_1$ is hydrogen, phenyl or a $C_1$-$C_{12}$-alkyl group.

6. The compound as claimed in claim 1, wherein X and Y are each a carbamyl radical selected from the group consisting of $C_1$-$C_{12}$-alkylcarbamyl, cyclohexylcarbamyl, allylcarbamyl, 2-($C_1$-$C_4$-alkoxy(-ethylcarbamyl, 3-($C_1$-$C_4$-alkoxy)-propylcarbamyl, 2-phenoxyethylcarbamyl, 3-phenoxypropylcarbamyl, phenylmethylcarbamyl, 2-phenylethylcarbamyl, phenylcarbamyl which is unsubstituted or substituted by chlorine, bromine, nitro and cyano; $C_1$-$C_4$-alkylphenylcarbamyl, dimethylphenylcarbamyl, trimethylphenylcarbamyl, $C_1$-$C_4$-dialkylcarbamyl, methylcyclohexylcarbamyl, dicyclohexylcarbamyl and a radical of the formula:

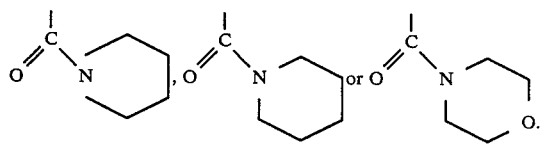

7. The compound as claimed in claim 1, wherein X and Y are each a carboxylic hydrazide radical having the formula:

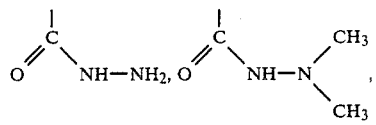
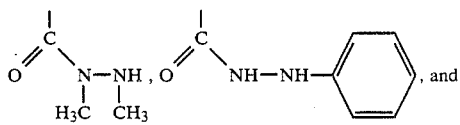
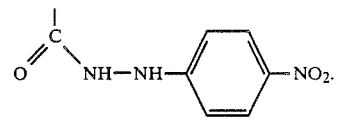
* * * * *